United States Patent [19]
Bonte et al.

[11] Patent Number: 5,955,083
[45] Date of Patent: Sep. 21, 1999

[54] **USE OF *ERIOBOTRYA JAPONICA* EXTRACT, IN PARTICULAR IN COSMETICS FOR STIMULATING GLYCOSAMINOGLYCAN SYNTHESIS**

[75] Inventors: Frédéric Bonte, Courbevoie; Marc Dumas, Colombes, both of France

[73] Assignee: LVMH Recherche, Nanterre, France

[21] Appl. No.: 08/894,701

[22] PCT Filed: Jan. 3, 1997

[86] PCT No.: PCT/FR97/00009

§ 371 Date: Aug. 28, 1997

§ 102(e) Date: Aug. 28, 1997

[87] PCT Pub. No.: WO97/06659

PCT Pub. Date: Feb. 27, 1997

[30] Foreign Application Priority Data

Jan. 3, 1996 [FR] France .................................. 96 00018

[51] Int. Cl.⁶ ..................................................... A61K 35/78
[52] U.S. Cl. ........................ 424/195.1; 435/371; 435/390
[58] Field of Search ......................... 424/195.1; 435/371, 435/390

[56] References Cited

FOREIGN PATENT DOCUMENTS

| | | |
|---|---|---|
| 62-067028 | 3/1987 | Japan . |
| 62-249907 | 10/1987 | Japan . |
| 63-115807 | 5/1988 | Japan . |
| 03188008 | 8/1991 | Japan . |
| 07215838 | 8/1995 | Japan . |

*Primary Examiner*—Jean C. Witz
*Attorney, Agent, or Firm*—Dennison, Meserole, Scheiner & Schultz

[57] ABSTRACT

The invention concerns novel uses of an *Eriobotrya japonica* extract, in particular in cosmetics or pharmaceutics. This extract permits stimulation of glycosaminoglycan synthesis, in particular of hyaluronic acid, thus imparting to the cosmetic compositions containing this extract the properties of improving the firmness and suppleness of the skin, combating the formation of wrinkles or lessening the depth thereof, smoothing the surface of the skin by means of a tightening effect, or moisturizing the skin. The invention further concerns the use of these extracts for stimulating the synthesis of glycosaminoglycans from a cell culture medium, in particular fibroblasts or keratinocytes.

18 Claims, No Drawings

USE OF *ERIOBOTRYA JAPONICA* EXTRACT, IN PARTICULAR IN COSMETICS FOR STIMULATING GLYCOSAMINOGLYCAN SYNTHESIS

The invention relates to a novel use of an extract of *Eriobotrya japonica*, especially in the field of cosmetics, as an agent for stimulating the synthesis of glycosaminoglycans.

The *Eriobotrya japonica* plant is a 5 to 7 m tall tree with glabrous branches and thick, oblong, alternate leaves, which flowers between the months of September and February. The leaves are recognized in the Vietnamese pharmacopeia for their antitussive and antispasmodic properties. The decoction is also used for washing wounds. According to the literature, this plant also possesses anti-inflammatory activities. Cosmetic activities on the hair or skin have also been mentioned.

The following may be mentioned more precisely as regards the already known applications of the *Eriobotrya japonica* plant in the field of pharmaceutics:

- the monograph concerning this plant in Chinese Herbal Medicine, page 296, which essentially indicates applications as an antitussive and as a gastric agent,
- the monograph on page 171 of Medicinal Plants in Vietnam, published under the aegis of the World Health Organization of Manilla and the Hanoi Institute of Medical Materials, which also mentions therapeutic applications as an antitussive and antispasmodic,
- Chinese Medicine Series 1, Chinese Materi Medica Vegetable Kingdom, which also mentions, on pages 164–165, applications of this same plant as an antitussive and antiemetic,
- Japanese patent JP 56-073027 (TEIJIN Ltd), which relates to applications of the leaves of this same plant to the preparation of an antiphlogistic.

More recently, applications of extracts of this same plant in the field of cosmetics have been described, particularly for skin or hair care.

Thus Japanese patent JP 05-017206 describes applications of extracts of this same plant as an agent for preventing or treating exfoliation of the epidermis in the case of rough skin, and demonstrates the activity of this plant on the reproduction of skin cells.

Japanese patent JP 62-249907 describes applications of *Eriobotrya japonica* leaves for the preparation of cosmetic products intended especially for improving the blood microcirculation.

Japanese patent JP 03-188008 describes applications in the field of cosmetics of a very broad family of plants, namely the rosaceae, these plants making it possible to improve the suppleness and moisturization of the skin and to treat papulae.

Japanese patent JP 03 188014 also describes cosmetic compositions intended especially for treating the hair and containing an extract of different plants from a very broad family of rosaceae. These plant extracts are associated with two particular surfactants, namely an anionic surfactant and at least one surfactant containing nitrogen.

It has now been discovered that extracts of the *Eriobotrya japonica* plant are of great value in cosmetics and pharmacy, especially in dermatology, by virtue of their property of stimulating the production of glycosaminoglycans by the fibroblasts and the keratinocytes, and particularly the fibroblasts of the dermis, especially of the human dermis, and human keratinocytes.

Now, those skilled in the art know that glycosaminoglycans (GAG) are polymers formed of disaccharide units.

Hyaluronic acid may be mentioned first of all among the GAG most frequently found in human skin, being present in the greatest abundance. Also present are chondroitin 4-sulfate and 6-sulfate, dermatan sulfate and, in small amounts, heparin and heparan sulfate.

The disaccharide units of GAG are formed of a hexosamine (D-glucosamine or D-galactosamine), fairly often sulfated, alternating with a uronic acid (D-glucuronic or L-iduronic acid).

GAG are generally covalently bonded to proteins to form proteoglycans. Among the known GAG, only hyaluronic acid, mentioned above, is not synthesized bonded to a central protein.

The structure of proteoglycans is described in the work by E. D. HAY entitled "Cell Biology of Extracellular Matrix", published by Plenum Press, New York in 1991, and in the publication by J. E. SILBERT entitled "Structure and Metabolism of Proteoglycans and Glycosaminoglycans", which appeared in J. Invest. Dermatol., 1982, 79, pages 31s–37s.

Proteoglycans are present in particular in all mammalian tissues, including the skin and its annexa (J. R. COUCHMAN, J. Invest. Dermatol. 1993 July 101 (1 Suppl.) 60S–64S). It is now acknowledged that proteoglycans contribute, via different processes, to the growth, preservation and repair of the tissues. It has been shown that some proteoglycans are mediators of cellular adhesion and transmembrane communication, while others interact with other structural elements of the extracellular matrix. As stated above, proteoglycans consist of a central protein to which one or more glycosaminoglycan chains are covalently bonded. Thus glycosaminoglycans are present in the dermis, participating in the composition of the extracellular matrix, and have been found bonded to certain sites of collagen fibers, as described by J. E. SCOTT in Int. J. Biol. Macromol., 1991, 13, pages 157–161. They have also been identified between the keratinocytes in the epidermis, as described by J. G. HAGGERTY et al. in the review J. Invest. Dermatol., 1992, 92, pages 374–380, 99 pages 374–380. Finally, glycosaminoglycans have been found in the extracellular matrix of the dermal papilla of the hair follicle. Their amount varies with the hair cycle. It reaches a maximum during the anagen phase, which corresponds to the growth of the hair. As far as the proteoglycans and glycosaminoglycans in the hair follicles are concerned, reference may be made in particular to the publication by J. R. COUCHMAN, op. cit., and to that by M. TAYLOR et al. entitled "Glycosaminoglycan synthesis by cultured human hair follicle dermal papilla cells: comparison with non-follicular dermal fibroblasts", Brit. J. Dermatol. 1992 (May) 126 (5) 479–84. It will be noted that it has been demonstrated that minoxidil, a well-known substance having a certain activity on hair growth and regrowth, stimulates the biosynthesis of glycosaminoglycans (Y. MORI et al., Ann. N.Y. Acad. Sci., 1991 (Dec. 26) 642 473–5). The observations of the authors cited above, combined with other clinical proofs, suggest that glycosaminoglycans participate in the regulation of hair growth.

Through their chief property of associating strongly with water molecules and forming gels, GAG ensure the moisturization of the dermis and epidermis. A well-moisturized skin guarantees a good appearance and a satisfactory physiological and functional state, with good mechanical properties in particular. The fact that GAG decrease in the course of skin ageing has been shown by numerous authors (for example: SMITH et al. in J. Invest. Dermatol., 1962, 39, pages 347–350; FLEISCHMAJER et al. in Biochim. Biophys. Acta, 1972, 279, pages 265–275; or LONGAS et al. in Carbohydr. Res., 1987, 159, pages 127–136).

It is therefore of interest to stimulate the synthesis of glycosaminoglycans, especially in order to give the qualities and properties of normal young skin to skin which exhibits a deficiency in terms of its mechanical properties or its water barrier, such as dehydrated or old skin, to prevent or treat hair growth disorders or to restore or improve the shine and suppleness of the hair.

Thus the main object of the present invention is to solve the novel technical problem which consists in providing a solution for stimulating the production of glycosaminoglycans by the skin cells, especially human skin cells such as the fibroblasts or the keratinocytes, which production is particularly valuable in the context of the manufacture of cosmetic or pharmaceutical treatment products, especially dermatological treatment products.

The invention is based on the unexpected discovery that an extract of the *Eriobotrya japonica* plant stimulates the production of glycosaminoglycans by the skin cells, particularly by the fibroblasts and the keratinocytes, thus being particularly useful for the manufacture of cosmetic or pharmaceutical treatment products, especially dermatological treatment products.

In particular, it has been discovered that the extract of *Eriobotrya japonica* stimulates the synthesis of hyaluronic acid by the fibroblasts and the keratinocytes.

Thus, according to one of its essential characteristics, the invention relates to the use of an extract of the *Eriobotrya japonica* plant as a cosmetic agent for stimulating the synthesis of glycosaminoglycans (GAG) by the skin cells, particularly by the fibroblasts and/or the keratinocytes, said cosmetic agent being incorporated in a cosmetically acceptable vehicle.

The invention relates more particularly to the applications in which this cosmetic agent is intended for stimulating the synthesis of hyaluronic acid by the fibroblasts and/or the keratinocytes, which proves to be particularly valuable for promoting the moisturization of the epidermis.

Examples which may be mentioned of extracts of *Eriobotrya japonica* which can be used according to the invention are commercial extracts, particularly the aqueous-ethanolic extract of leaves of this plant, which is listed in the catalog of Maruzen Pharmaceutical, Hiroshima, Japan.

In one advantageous embodiment of the invention, the plant extract is obtained from the ground aerial parts of the *Eriobotrya japonica* plant, preferably from leaves, flowers, stems, stem bark or fruits.

In another preferred embodiment, the above-mentioned extract is an extract of ground leaves of the *Eriobotrya japonica* plant.

In yet another advantageous embodiment, the above-mentioned extract of the *Eriobotrya japonica* plant is an extract obtained by extraction with a polar solvent or a mixture of polar solvents. It will be preferable to use an alcohol such as methanol, ethanol, propanol, isopropanol, propylene glycol or butylene glycol, a mixture of these alcohols or an aqueous-alcoholic mixture.

1,3-Butylene glycol or a mixture of this solvent with water, preferably a 50:50 mixture by volume, will advantageously be chosen as the solvent for carrying out this extraction.

The conventional extraction procedures well known to those skilled in the art can be used in this context. In particular, the extraction can be carried out on the ground material, preferably on the aerial parts such as leaves, flowers, stems, stem bark or fruits. The extraction is advantageously carried out on leaves. The ground plant material is introduced into the extraction solvent, which preferably consists of the above-mentioned polar solvent or mixture of polar solvents. The extraction can be repeated several times until the material is exhausted, as practiced in the processes well known to those skilled in the art. The extraction can be carried out at room temperature or under the action of heat, especially at the reflux point of the solvent. The weight ratio of the solvent to the material to be extracted can vary within wide limits. More precisely, it can be between 1:1 and 50:1 and preferably between 5:1 and 20:1.

It has furthermore been observed that the stimulation of glycosaminoglycan synthesis has a slight swelling effect on the skin, particularly on the dermis, and consequently affords different advantageous cosmetic results such as an improvement in skin firmness, the prevention of wrinkles or their reduction through a decrease in their depth, and the smoothing of the skin surface through an underlying tightening effect.

Furthermore, the improvement in GAG synthesis contributes to an improvement in the moisturization of the skin.

Therefore, according to another essential characteristic, the invention further relates to a method of cosmetic or pharmaceutical treatment, especially dermatological treatment, for stimulating glycosaminoglycan (GAG) synthesis, particularly hyaluronic acid synthesis, characterized in that it comprises the application of a cosmetically or pharmaceutically effective amount, especially a dermatologically effective amount, of an extract of the *Eriobotrya japonica* plant in order to stimulate said synthesis, said extract being contained particularly in a cosmetically or pharmaceutically acceptable excipient, especially a dermatologically acceptable excipient. Thus the invention makes it possible to improve the firmness and suppleness of the skin, to combat the formation of wrinkles or reduce their depth, to smooth the skin surface through a tightening effect or to improve the moisturization of the skin.

The invention further relates to any method of therapeutic treatment of the skin by which it is desired to stimulate glycosaminoglycan synthesis, particularly hyaluronic acid synthesis.

The invention further relates to the use of extracts of *Eriobotrya japonica* for the preparation of pharmaceutical compositions, especially dermatological compositions, for the treatment of subjects suffering from an insufficiency of glycosaminoglycan synthesis, particularly of hyaluronic acid synthesis, in order to correct the adverse effects of said insufficiency and in particular to improve the firmness and suppleness of the skin, to combat the formation of wrinkles or reduce their depth, to smooth the skin surface through a tightening effect or to improve the moisturization of the skin.

These extracts and compositions can be used in any method of cosmetic or therapeutic treatment in which it is desired to stimulate GAG synthesis. These methods consist in applying a cosmetically or pharmaceutically effective amount of said extract, or of the composition in which they are present, to the skin tissue to be treated in order to stimulate said synthesis, said extract optionally being included in a cosmetically or pharmaceutically acceptable vehicle.

Various types of formulation can be prepared. One of the most widely used forms is a topical form suitable for application to the skin tissue, including the skin and the external or internal mucosa. The appropriate topical formulations include, without limitation, emulsions, creams, milks, balms, gels, lotions, pessaries and treating make-up compositions such as mascaras and lipsticks, these different types of formulation being well known to those skilled in the art.

These compositions contain from 0.001% to 10% by weight and preferably 0.01% to 5% by weight, based on the total weight of said composition of said extract, said extract preferably being incorporated in a cosmetically or pharmaceutically acceptable excipient.

These compositions may also contain different additives, particularly additives selected from the group comprising retinoids, humectants or moisturizers, vitamins, ceramides, collagen synthesis promoters and amino acids.

In these modified embodiments, the above-mentioned retinoid is selected from retinoic acid and its salts and esters, retinaldehyde, and retinol and its esters such as the propionate, palmitate and acetate; the above-mentioned humectant or moisturizer is selected from glycerol, a polyethylene glycol and hyaluronic acid; the above-mentioned vitamin is selected from vitamin A, vitamin C and its derivatives, particularly its sodium or magnesium salts, vitamin E, vitamin PP and the B group vitamins, particularly B6 and B12; the collagen synthesis promoter is selected from an extract of *Centella asiatica*, madecassoside, madecassic acid, asiatic acid and asiaticoside; and the amino acid is selected from serine, threonine, aspartic acid, leucine, lysine, proline and hydroxyproline.

In the compositions of the invention, the extract of *Eriobotrya japonica* may also advantageously be associated with one or more of the following active principles:

a hyaluronidase inhibitor such as an extract of *Echinacea angustifolia*, an elastase inhibitor such as a soya extract or an alga extract called aosaine, an amino sugar such as glucosamine or galactosamine, an adenylate cyclase activator promoting $AMP_c$ synthesis, such as forskolin, an extract of *Coleus forskholii* or an extract of Tephrosia, $AMP_c$ or an extract containing it, such as an extract of Taisoh, a phosphodiesterase inhibitor counteracting the degradation of $AMP_c$, such as caffeine or theophylline.

Finally, according to a last feature, the present invention further relates to a process for the treatment of cells, particularly fibroblasts or keratinocytes, in culture, with an effective concentration of an extract of *Eriobotrya japonica* in order to stimulate glycosaminoglycan synthesis, particularly hyaluronic acid synthesis.

Thus, for example, in the context of the preparation of artificial skin, particularly artificial dermis, by cell culture using the techniques well known to those skilled in the art, the process of the invention provides an artificial skin or dermis of very good quality, particularly as regards the biomechanical properties.

In one preferred modified mode of carrying out the above-mentioned process, the cell culture is treated with an extract of *Eriobotrya japonica* at a concentration of between 0.3 μg/ml and 30 μg/ml of culture medium.

In another advantageous modified mode, the culture medium also comprises one or more of the following substances: glucosamine, galactosamine, L-proline and 4-hydroxy-L-proline, it being possible for each of said substances to be present at a concentration of between 2 and 10 mM, or alternatively the culture medium can contain ascorbic acid or one of its derivatives at a non-cytotoxic concentration, particularly of between 0.001 mM and 0.5 mM.

Other objects, characteristics and advantages of the invention are also clearly apparent to those skilled in the art from the following explanatory description referring to several Examples, which are given simply by way of illustration and which cannot under any circumstances limit the scope of the invention. The percentages in the Examples are given by weight, unless indicated otherwise.

EXAMPLES

I—Preparation of extracts of aerial parts of Eriobotrya

Example 1

Preparation of an extract A 1 kg of leaves of the plant is ground and then brought into contact with 10 liters of methanol under reflux. The extract is filtered. The plant residue is then re-extracted twice by the same process. The filtrates are combined and concentrated to give a dry extract called A.

Example 2

Preparation of an extract B

The procedure is as in Example 1 except that a 50/50 v/v water-ethanol mixture is used as the extraction solvent.

Example 3

Preparation of an extract C

An extraction phase is prepared in the following manner. 1 kg of leaves of the plant is ground and then brought into contact with 15 liters of methanol. The mixture is subsequently refluxed for 30 minutes and then filtered. The residue is then re-extracted twice with 15 liters of methanol, as in Example 1.

The different filtrates are recovered. They are concentrated to the solubility minimum. The concentrate is then mixed with 5 volumes of acetone. The precipitate is washed with acetone until the visual coloration has disappeared. The cake obtained is then suspended in water to give a homogeneous milk, which is lyophilized to give a lyophilizate called extract C.

Example 4

Preparation of an extract D 1 kg of dry leaves of the plant, ground beforehand, is extracted with 15 to 20 l of a 50/50 by volume mixture of 1,3-butylene glycol and water at 35° C. for 1 h, with agitation. A suspension is recovered which is filtered to give an extract called D.

II—Demonstration of the stimulating activity on glycosaminoglycan production

Example 5

Demonstration of the stimulating activity on glycosaminoglycan production by human fibroblasts with the extract of Example 1

The test used to demonstrate a stimulating activity on GAG production by fibroblasts is described below. This in vitro test is recognized in other connections as being reliable and significant for those skilled in the art.

Test protocol

Fibroblasts originating from a mammaplasty carried out on a 49-year-old woman are prepared from the microdissected dermis as described by R. I. Freshney, Culture of animal cells; A manual of basic technique, A. R. Liss, New York, 1983, 104–106.

10,000 fibroblasts per culture well of a multiwell dish (6 wells per dish) are inoculated for 24 h at 37° C. into an E199 C culture medium (Gibco) containing 10% of fetal calf serum.

After 24 h, the medium is withdrawn and replaced with 100 microliters of serum-free E199 C medium containing the test product solubilized in DMSO, or the same amount of DMSO in the case of the "control" cultures, and 4 $\mu$Ci of $^3$H-glucosamine (ref. TRK 398 Amersham). Incubation is carried out for 48 h at 37° C. Then the supernatants are removed, combined in groups of 2 and transferred to screw-threaded Eppendorf tubes. 200 $\mu$l of a solution containing 0.2 mg/ml of pronase (Sigma P5147) in PBS containing 0.02% of sodium nitride are added to each tube. The reaction is allowed to proceed overnight at 37° C. The pronase is then inactivated by immersion of the tubes in boiling water for 5 min.

After cooling to room temperature, the radiolabeled GAG are coprecipitated with an aqueous solution containing 8 mg/ml of a 1/1/1 mixture of hyaluronic acid, dermatan sulfate and chondroitin sulfate by means of 40 $\mu$l of a solution containing 100 mg/ml of CPC (Sigma C 9002). The resulting mixture is shaken and left to incubate for 30 min at room temperature. The precipitate is centrifuged, the supernatant is sucked off and the residue is recovered with 400 $\mu$l of a solution containing 10 mg/ml of CPC. The mixture is shaken for 5 min and the residue is taken up with 500 $\mu$l of methanol. The mixture is shaken and transferred to scintillation bottles, 10 ml of liquid scintillator are then added and the radioactivity is counted.

In a parallel experiment, the cytotoxicity of the test product is evaluated by an XTT (tetrazolium salt) test as described by Roehm N. W. et al. in Journal of Immunological Methods 1991, 142, 257–265. This test measures the cellular viability. The activity results are given only for concentrations which do not modify the cellular viability.

Results:

|  | Amount of GAG expressed in cpm | % activity | Significance |
| --- | --- | --- | --- |
| Control | 6977 ± 771 | | |
| 2.5 $\mu$g/ml | 11808 ± 647 | +69 | S |
| 10 $\mu$g/ml | 12764 ± 734 | +83 | S |

The above Table clearly demonstrates that the extract tested stimulates the production of total GAG by human dermal fibroblasts.

Example 6

Demonstration of the stimulating activity on glycosaminoglycan production by human fibroblasts on a commercial extract An experiment such as that described in Example 5 is carried out using a commercial 50/50 by volume ethanol-water extract from Maruzen (Japan).

This extract was tested blind. It was lyophilized and then taken up with DMSO to give a stock solution containing 10 mg/ml, which was tested on the same strain of fibroblasts as that used in Example 5, under the same conditions. It was observed that a solution containing 10 $\mu$g/ml stimulates GAG synthesis by more than 22.5%, expressed in cpm.

III—Application Examples

Example 7

Cosmetic cream for improving the firmness of the skin:
alcoholic extract C of Eriobotrya leaves according to Example 3 ...... 2 g
extract of *Centella asiatica* 0.5 g
perfumed excipient qsp 100 g This cream is applied topically to the face, neck and bust. This composition also improves the suppleness of the skin.

Example 8

Gel for providing a tightening effect on the skin:
glycolic extract D of *Eriobotrya japonica* leaves obtained in Example 4 3 g
ascorbic acid salt of magnesium phosphate 1 g
asiaticoside 0.1 g
perfumed gelled excipient with preservatives qsp 100 g This gel is applied locally to the face.

Example 9

Lotion for enhancing the tonicity of the dermis and reducing the depth of the wrinkles:
glycolic extract of *Eriobotrya japonica* leaves obtained according to Example 4 0.8 g
extract of panax ginseng 0.2 g
extract of capsicum 0.01 g
perfumed aqueous excipient qsp 100 g This lotion is sprayed on, in a preventive capacity, after washing.

Example 10

Anti-wrinkle cream:
glycolic extract of *Eriobotrya japonica* leaves according to Example 4 2 g
AMP$_c$ 0.05 g
extract of Taisoh 1 g
theophylline 0.1 g
emulsified excipient with perfume and preservatives qsp 100 g This cream, applied daily, improves the structure of the dermis and restores firmness and tonicity to the skin.

We claim:

1. A method for stimulating glycosaminoglycan (GAG) synthesis in a human in need thereof, comprising delivering tonically to the skin of the human an extract of the *Eriobotrya japonica* plant in an amount effective to stimulate said synthesis, the extract of the *Eriobotrya japonica* plant being in combination with at least one active principle selected from the group consisting of a hyaluronidase inhibitor, an elastase inhibitor, an amino sugar, an adenylate cyclase activator promoting AMP$_c$ synthesis, AMP$_c$ or an extract containing AMP$_c$ and a phosphodiesterase inhibitor counteracting the degradation of AMP$_c$, said extract being optionally contained in a cosmetically or pharmaceutically acceptable excipient.

2. A method according to claim 1, wherein the hyaluronidase inhibitor is an extract of *Echinacea angustifolia*; the elastase inhibitor is a soya extract or an alga extract called aosaine; the amino sugar is glucosamine or galactosamine; the adenylate cyclase activator promoting AMP$_c$ synthesis is forskolin, an extract of *Coleus forskholii* or an extract of *Tephrosia*; the AMP$_c$ or extract containing AMP$_c$ is an extract of Taisoh; and the phosphodiesterase inhibitor counteracting the degradation of AMP$_c$ is caffeine or theophylline.

3. A method for the treatment of skin cells selected from the group consisting of fibroblasts and keratinocytes, by culture in a culture medium containing said skin cells for stimulating glycosaminoglycan synthesis by said cells, comprising introducing into the culture medium an extract of *Eriobotrya japonica* in an amount effective to stimulate said glycosaminoglycan synthesis by said cells.

4. A method according to claim 3, wherein said cells are treated with an extract of *Eriobotrya japonica* at a concentration of between 0.3 µg/ml and 30 µg/ml of culture medium.

5. A method according to claim 4, comprising further adding to the culture medium at least one substance selected from the group consisting of glucosamine, galactosamine, L-proline, 4-hydroxyl-L-proline, ascorbic acid and ascorbic acid compounds.

6. A method according to claim 5, wherein said culture medium contains at least one substance selected from the group consisting of glucosamine, galactosamine, L-proline and 4-hydroxyl-L-proline at a concentration between 2 and 10 mM.

7. A method according to claim 5, wherein said ascorbic acid and ascorbic acid compounds are present at a non-cytotoxic concentration.

8. In a method for preparation of an artificial skin or dermis by culture of skin or dermis cells selected from the group consisting of fibroblasts and keratinocytes in a culture medium, the improvement comprising introducing into said culture medium an extract of *Eriobotrya japonica* in an amount effective to stimulate glycosaminoglycan synthesis by said cells.

9. A method according to claim 8, wherein the extract of *Eriobotrya japonica* is present at a concentration between 0.3 µg/ml and 30 µg/ml of the culture medium.

10. A composition to be applied topically on the skin of a human, comprising an extract of the *Eriobotrya japonica* plant in combination with at least one active principle selected from the group consisting of a hyaluronidase inhibitor, an elastase inhibitor, an amino sugar, an adenylate cyclase activator promoting $AMP_c$ synthesis, $AMP_c$ or an extract containing $AMP_c$, and a phosphodiesterase inhibitor counteracting the degradation of $AMP_c$, optionally contained in a cosmetically or pharmaceutically acceptable excipient.

11. The composition of claim 10, wherein the hyaluronidase inhibitor is an extract of *Echinacea angustifolia*; the elastase inhibitor is a soya extract or an alga extract called aosaine; the amino sugar is glucosamine or galactosamine; the adenylate cyclase activator promoting $AMP_c$ synthesis is forskolin, an extract of *Coleus forskholii* or an extract of Tephrosia; the $AMP_c$ or an extract containing AMPc is an extract of Taisoh; and the phosphodiesterase inhibitor counteracting the degradation of $AMP_c$ is caffeine or theophylline.

12. The composition of claim 10, wherein said extract is present in said composition in a concentration of between 0.001% and 10% by weight of said composition.

13. The composition of claim 12, wherein said extract of *Eriobotrya japonica* is present in said composition at a concentration ranging between 0.01% and 5% by weight of said composition.

14. A composition to be applied topically on the skin of a human, comprising an extract of the plant *Eriobotrya japonica* in a concentration of between of 0.001% and 10% by weight of said composition, in combination with at least one $AMP_c$ active principle selected from the group consisting of $AMP_c$ or an extract containing $AMP_c$, an adenylate cyclase activator promoting $AMP_c$ synthesis and a phosphodiesterase inhibitor counteracting the degradation of $AMP_c$.

15. The composition of claim 14, wherein the adenylate cyclase activator promoting $AMP_c$ synthesis is forskolin, an extract of *Coleus forskholii* or an extract of Tephrosia, the $AMP_c$ or an extract containing $AMP_c$ is an extract of Taisoh and the phosphodiesterase inhibitor counteracting the degradation of $AMP_c$ is caffeine or theophylline.

16. A cosmetic composition to be topically applied on the skin of a human, comprising an extract of the *Eriobotrya japonica* plant in a concentration of between 0.001% and 10% by weight of said composition, in combination with at least one of $AMP_c$, an extract of Taisoh and theophylline, or caffeine, in a cosmetically or pharmaceutically acceptable excipient.

17. The composition of claim 16, wherein said extract of *Eriobotrya japonica* is a glycolic extract of *Eriobotrya japonica* leaves in a concentration of about 2% by weight of said composition, said $AMP_c$ is at a concentration of about 0.05% by weight of said composition, said extract of Taisoh is at a concentration of about 1% by weight of said composition, and said theophylline is at a concentration of about 0.1% by weight of said composition, in a cosmetically or pharmaceutically acceptable excipient.

18. The composition of claim 17, which is an anti-wrinkle cream thereby improving the structure of the dermis and restoring firmness and tonicity to the skin.

* * * * *